(12) United States Patent
Yuan et al.

(10) Patent No.: US 11,779,442 B2
(45) Date of Patent: Oct. 10, 2023

(54) TEETH CLEANING APPARATUS

(71) Applicant: XIAMEN JIEBOYA TECHNOLOGY CO. LTD., Fujian (CN)

(72) Inventors: Mu Yuan, Fujian (CN); Caibo Gu, Fujian (CN)

(73) Assignee: XIAMEN JIEBOYA TECHNOLOGY CO, LTD., Fujian (CN)

( * ) Notice: Subject to any disclaimer, the term of this patent is extended or adjusted under 35 U.S.C. 154(b) by 1219 days.

(21) Appl. No.: 16/378,571

(22) Filed: Apr. 9, 2019

(65) Prior Publication Data

US 2020/0179088 A1    Jun. 11, 2020

(30) Foreign Application Priority Data

Dec. 5, 2018 (CN) .......................... 201811481174.9

(51) Int. Cl.
*A61C 17/02* (2006.01)
*A61C 1/00* (2006.01)
*A61K 8/22* (2006.01)
*A61H 13/00* (2006.01)

(52) U.S. Cl.
CPC ........ *A61C 17/0202* (2013.01); *A61C 1/0015* (2013.01); *A61C 1/0092* (2013.01); *A61K 8/22* (2013.01); *A61C 2204/002* (2013.01); *A61H 13/005* (2013.01)

(58) Field of Classification Search
CPC .............. A61C 17/0202; A61C 1/0015; A61C 1/0092; A61C 2204/002; A61C 17/0217; A61C 17/02; A61K 8/22; A61H 13/005
See application file for complete search history.

(56) References Cited

U.S. PATENT DOCUMENTS

| 2006/0078844 | A1* | 4/2006 | Goldman | ............... A61C 17/36 601/162 |
| 2014/0272782 | A1* | 9/2014 | Luettgen | ............ A61C 17/0205 433/80 |
| 2017/0367800 | A1* | 12/2017 | Challa | ................ A61C 17/0205 |
| 2018/0000572 | A1* | 1/2018 | Johanski | ............ A61C 17/0202 |
| 2018/0279761 | A1* | 10/2018 | Haddad | ................ A46B 15/003 |

* cited by examiner

*Primary Examiner* — Quang D Thanh
(74) *Attorney, Agent, or Firm* — JCIP GLOBAL INC.

(57) ABSTRACT

Disclosed is a teeth cleaning apparatus, including a first liquid reservoir, a teeth cleaner, a connector, and a liquid conveyer. The teeth cleaner includes a teeth cleaner body and a second liquid reservoir that is fixedly connected to the teeth cleaner body and transmits a teeth cleaning liquid to the teeth cleaner body during teeth cleaning. The connector is separable from the teeth cleaner, and the liquid conveyer transmits the teeth cleaning liquid in the first liquid reservoir to the second liquid reservoir when the teeth cleaner is connected on the connector.

17 Claims, 7 Drawing Sheets

TEETH CLEANING APPARATUS

CROSS-REFERENCE TO RELATED APPLICATION

This application claims the priority benefit of China application serial no. 201811481174.9, filed on Dec. 5, 2018. The entirety of the above-mentioned patent application is hereby incorporated by reference herein and made a part of this specification.

BACKGROUND OF THE INVENTION

1. Field of the Invention

This application relates to the field of personal hygiene care, and more specifically, to a teeth cleaning apparatus.

2. Description of Related Art

It is known that supplying ozone water as a teeth cleaning liquid to a teeth cleaner helps cleaning teeth. In the existing technology, to clean teeth with ozone water, a water tank needs to be disposed. An ozone generator is disposed in the water tank. The water tank is connected to the teeth cleaner through a pump. During teeth cleaning, water is first electrolyzed in the water tank to generate ozone, and then water carrying ozone is transmitted to the teeth cleaner through the pump and ejected to teeth, thereby achieving the function of cleaning teeth. However, in the foregoing technical solution, the pump and the water tank are fixedly connected in a case. During teeth cleaning, to ensure that the pump is in communication with a pipe of the teeth cleaner, a hose needs to be connected between the teeth cleaner and the case. The hose restricts poses in which a user holds the teeth cleaner, resulting in inconvenience in the teeth cleaning process. In addition, the hose further needs to be stored after the teeth cleaning is finished, which causes poor using experience. Definitely, the teeth cleaning liquid is not limited to the ozone water. When people use other disinfection liquids or even filtered purified water as the teeth cleaning liquid, the water tank also needs to be used to prepare or filter the teeth cleaning liquid. In this case, the foregoing technical defect also exists.

SUMMARY OF THE INVENTION

The following is a summary of the subject that is described in detail in this text. The summary is not intended to limit the protection scope of the claims.

This application provides a teeth cleaning apparatus, which can allow a user to hold a teeth cleaner freely to obtain good using experience when a water tank needs to be mounted to generate or store a teeth cleaning liquid.

Embodiments of this application relate to a teeth cleaning apparatus, including: a first liquid reservoir, used for storing a teeth cleaning liquid; a teeth cleaner, including a teeth cleaner body and a second liquid reservoir fixedly connected to the teeth cleaner body, the second liquid reservoir transmitting the teeth cleaning liquid to the teeth cleaner body during teeth cleaning, and the second liquid reservoir being further provided with a check valve that is opened when the teeth cleaning liquid is injected into the second liquid reservoir; a connector, which is separated from the teeth cleaner during teeth cleaning, and allows the teeth cleaner to be connected thereon after teeth cleaning, the connector being provided with a liquid feeding nozzle, and the liquid feeding nozzle being in communication with the second liquid reservoir through the check valve when the connector is connected to the teeth cleaner; and a liquid conveyer, used for transmitting the teeth cleaning liquid in the first liquid reservoir to the second liquid reservoir through the liquid feeding nozzle.

BRIEF DESCRIPTION OF THE DRAWINGS

To describe the technical solutions in the embodiments of this application more clearly, the following briefly introduces the accompanying drawings required for describing the embodiments. Apparently, the accompanying drawings in the following description show some embodiments of this application, and a person of ordinary skill in the art may still derive other drawings from these accompanying drawings without creative efforts.

DESCRIPTION OF THE EMBODIMENTS

The technical solutions in the embodiments of this application are described in the following with reference to the accompanying drawings in the embodiments of this application.

Embodiment 1

Figure 1:
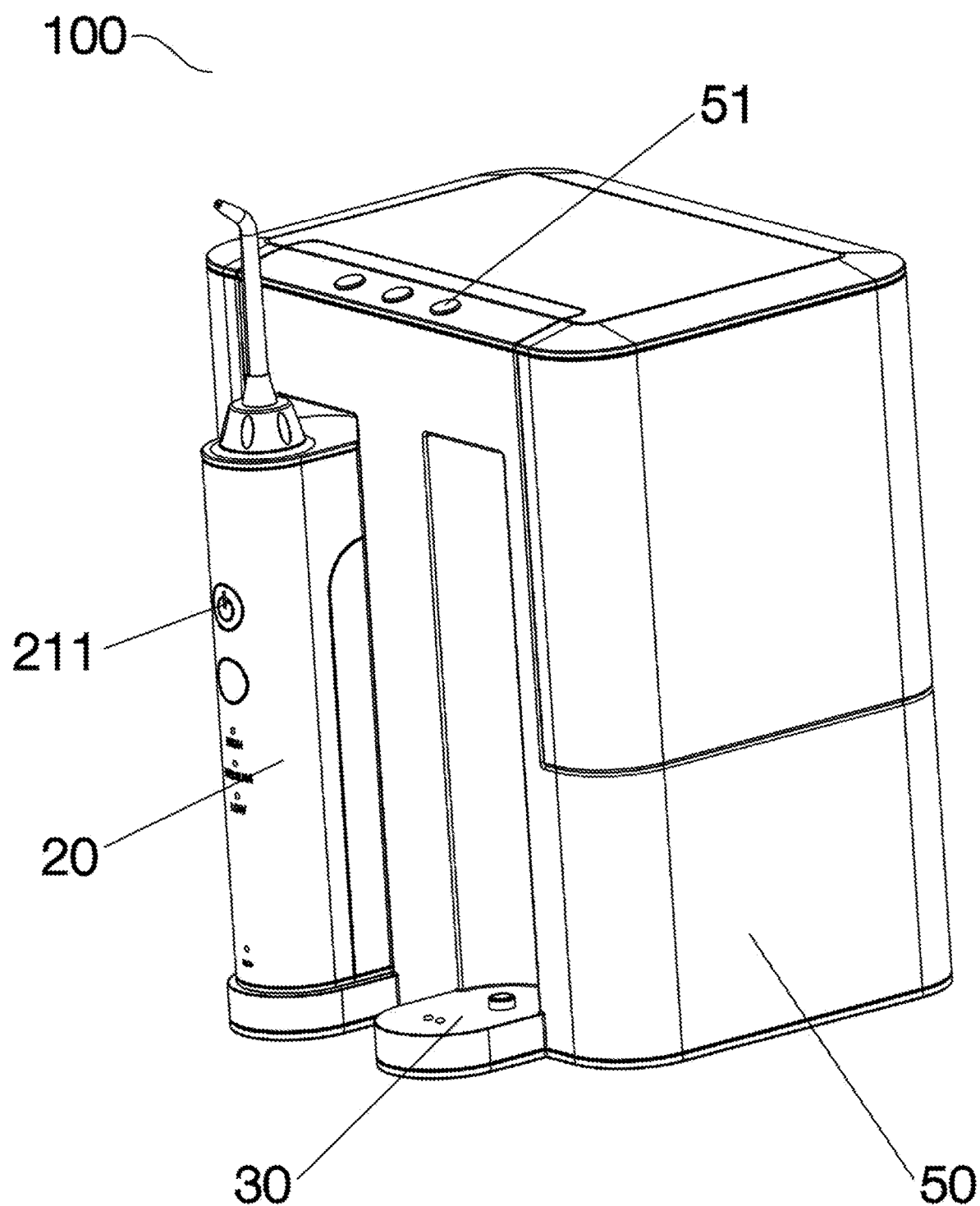
FIG. 1 is a three-dimensional diagram of a teeth cleaning apparatus when a teeth cleaner is connected to a connector in Embodiment 1.
Figure 2:
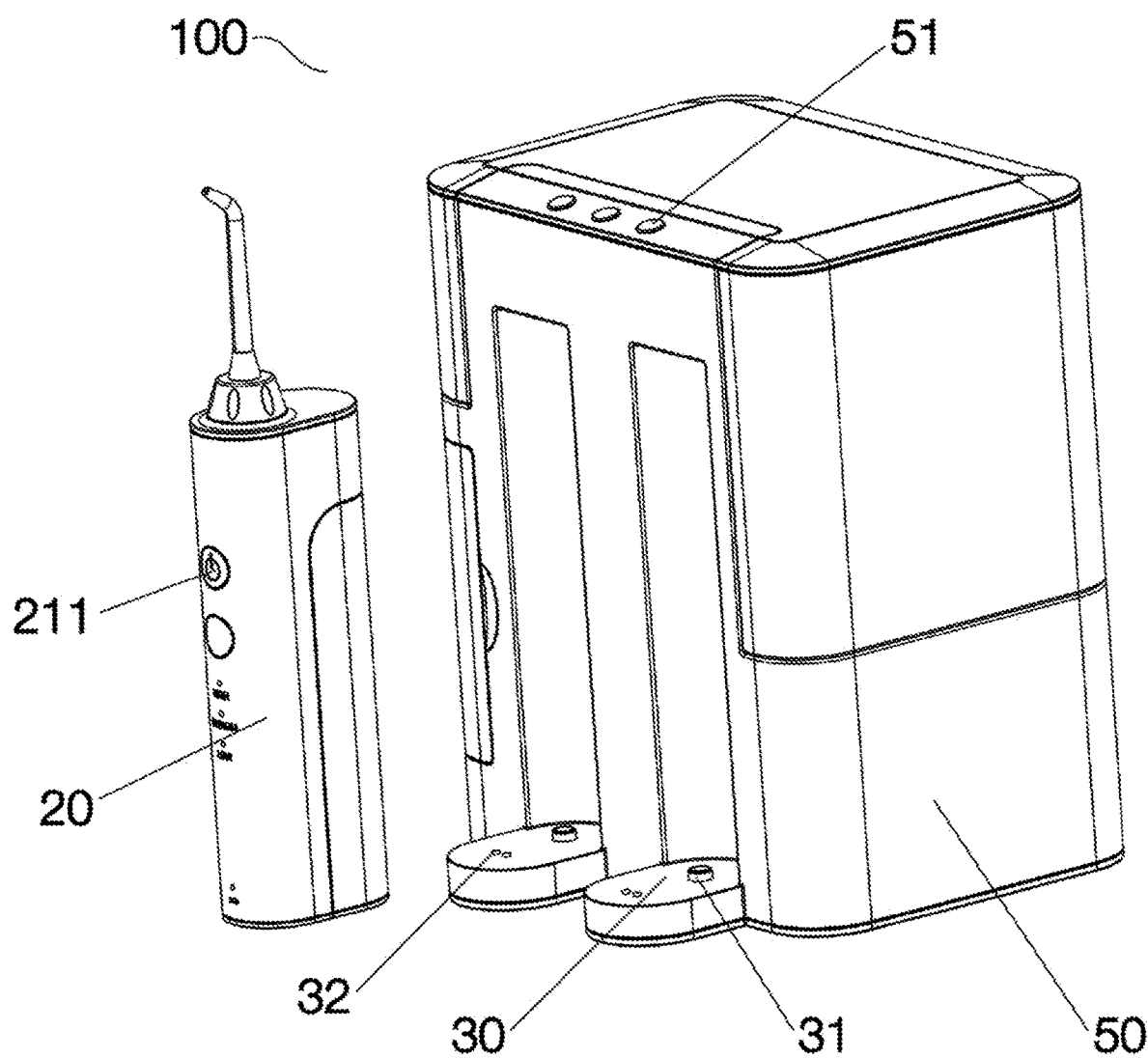
FIG. 2 is a three-dimensional diagram of the teeth cleaning apparatus when the teeth cleaner is separated from the connector in Embodiment 1.
Figure 3:
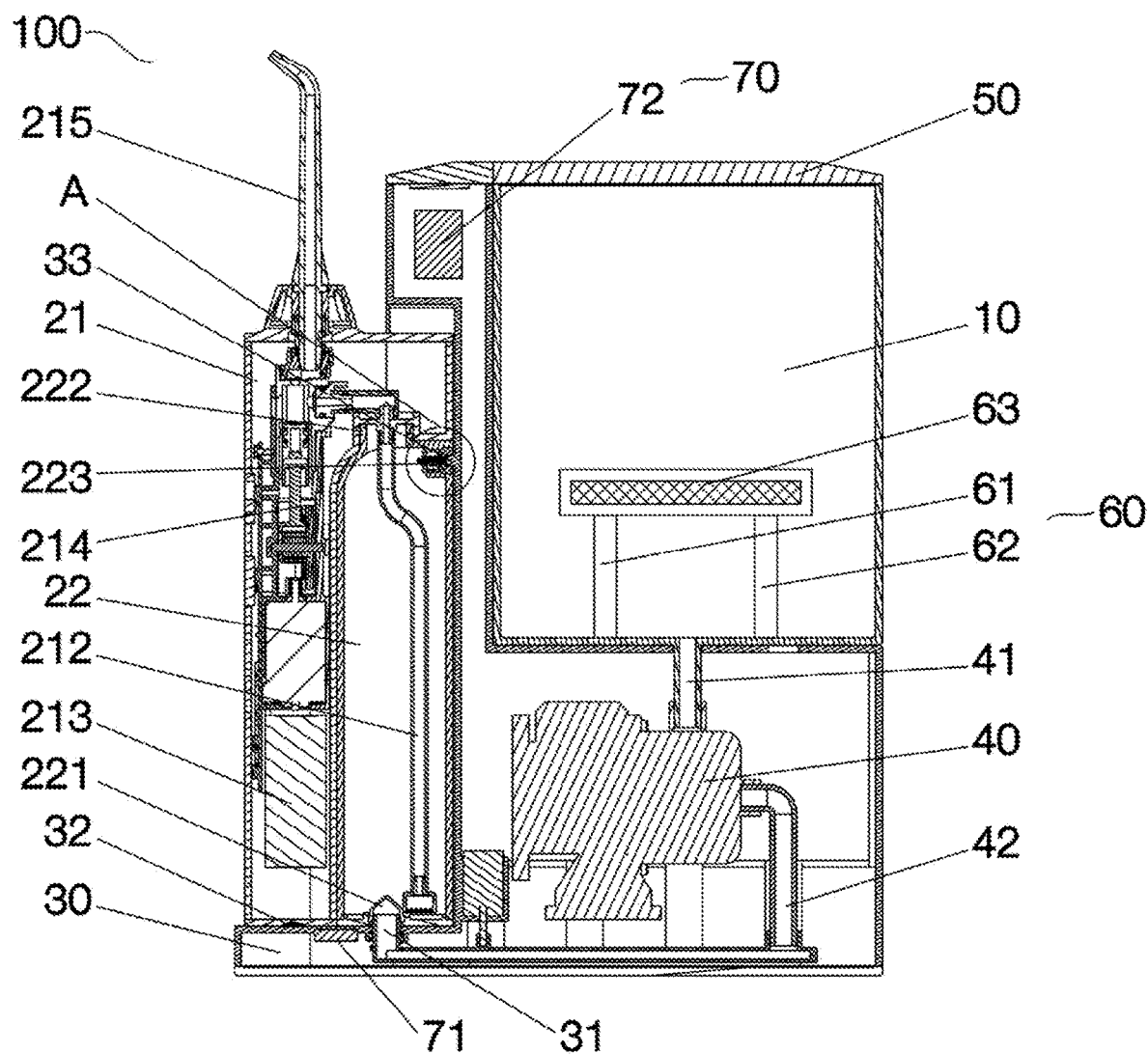
FIG. 3 is a schematic structural diagram of the teeth cleaning apparatus in Embodiment 1.

Referring to FIG. 1 to FIG. 4, as shown in FIG. 3, in Embodiment 1, a teeth cleaning apparatus 100 includes a first liquid reservoir 10, a teeth cleaner 20, a connector 30, a liquid conveyer, a housing 50, an ozone generator 60, and a controller 70.

The first liquid reservoir 10 is disposed in the housing 50 and is used for storing water, so that a teeth cleaning liquid containing ozone is generated by using the ozone generator 60 and stored in the first liquid reservoir 10.

The teeth cleaner 20 includes a teeth cleaner body 21 and a second liquid reservoir 22 fixedly connected to the teeth cleaner body 21.

The teeth cleaner body 21 includes a casing, a switch 211 disposed on the casing, a liquid suction pipe 212 inserted into the second liquid reservoir 22, a rechargeable battery 213, a liquid suction device 214, an ejector 215, and a power receiving terminal disposed at a bottom portion of the casing. The switch 211 is used for controlling the liquid suction device 214 to be turned on and turned off. The liquid suction pipe 212, the liquid suction device 214, and the ejector 215 are in communication in sequence, to suck the teeth cleaning liquid in the second liquid reservoir 22, and the sucked teeth cleaning liquid is ejected by the ejector 215. The power receiving terminal is electrically connected to the rechargeable battery 213.

Figure 4:
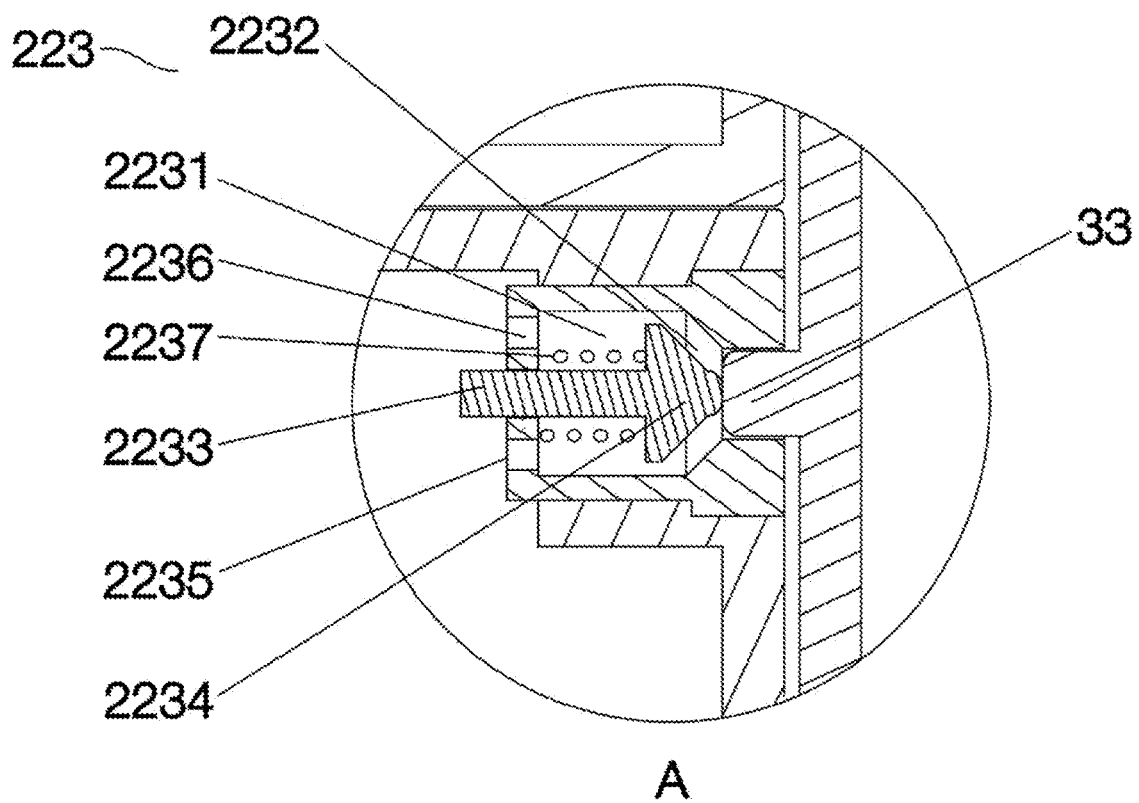
FIG. 4 in an enlarged view of part A in FIG. 3, and shows an exhaust structure and an exhaust driving structure in Embodiment 1.

The second liquid reservoir 22 is clamped on a backside of the teeth cleaner body 21, and is detachable from the teeth cleaner body 21. When the teeth cleaner 20 is used to clean teeth, the second liquid reservoir 22 supplies the teeth cleaning liquid to the teeth cleaner body 21. The second liquid reservoir 22 includes a tank body, a check valve 221 disposed at a bottom portion of the tank body, and an air inlet 222 and an exhaust structure 223 that are provided at an upper portion of the tank body. A known duckbill valve is used as the check valve 221 at the bottom portion of the tank body. Definitely, any other type of check valve may be used, as long as it can be ensured that the check valve is open when the teeth cleaning liquid is injected into the second liquid reservoir 22. The air inlet 222 is used for sucking air therein when the second liquid reservoir 22 transmits the teeth cleaning liquid to the teeth cleaner body 21, so that the teeth cleaning liquid can be transmitted from the second liquid reservoir 22 to the teeth cleaner body 21 smoothly. The air inlet 222 has a relatively small opening with a diameter of 0.5 mm approximately. Due to surface tension of the teeth cleaning liquid and an atmospheric pressure, the teeth cleaning liquid in the second liquid reservoir 22 cannot flow out of the second liquid reservoir 22. As shown in FIG. 4, the exhaust structure 223 includes an exhaust passage 2231 provided with an exhaust hole 2232, a slide bar 2233 slidably disposed in the exhaust passage 2231, a plug head 2234 fixedly connected at one end of the slide bar 2233 and used for blocking the exhaust hole 2232, and an elastic piece 2237 for driving the plug head 2234 to block the exhaust hole 2232. The elastic piece 2237 is configured as a spring in the present embodiment. The exhaust hole 2232 is located at an outer end of the exhaust passage 2231. The exhaust passage 2231 is provided with a stopping wall 2235 at an end close to an interior portion of the tank body. The stopping wall 2235 is further provided with a through hole 2236 allowing air to flow in and out. The slide bar 2233 penetrates the stopping wall 2235. The elastic piece 2237 is sleeved over the slide bar 2233. One end of the elastic piece 2237 abuts against the plug head 2234 and the other end of the elastic piece 2237 abuts against the stopping wall 2235. The exhaust structure 223 can exhaust air when the teeth cleaning liquid is injected into the second liquid reservoir 22 or when the teeth cleaner 20 is placed on the connector 30, so that the teeth cleaning liquid can be injected quickly.

The connector 30 is disposed at a notch of the housing 50. In the present embodiment, there are two connectors 30, which are both in the form of a connecting seat, so that the teeth cleaner 20 can be placed thereon. The connector 30 is provided with a liquid feeding nozzle 31 and a charging terminal 32. The liquid feeding nozzle 31 is in communication with the second liquid reservoir 22 through the check valve 221 when the teeth cleaner 20 is connected to the connector 30. The charging terminal 32 is electrically connected to a power supply, so that the teeth cleaner 20 is electrically connected to the rechargeable battery 213 through the power receiving terminal when the teeth cleaner 20 is placed on the connecting seat. Moreover, the charging terminal 32 charges the rechargeable battery 213, and a user does not need to additionally bother to charge the teeth cleaner body 21. In the present embodiment, an external wall of the housing 50 further forms a sidewall of the connector 30. As shown in FIG. 4, the sidewall of the connector 30 is provided with an exhaust driving structure. In the present embodiment, the exhaust driving structure is a projection 33.

In the present embodiment, the liquid conveyer is a liquid pump 40, which is disposed in the housing 50 and located below the first liquid reservoir 10. The liquid pump 40 is used for transmitting the teeth cleaning liquid in the first liquid reservoir 10 to the liquid feeding nozzle 31. A liquid inlet end of the liquid pump 40 is in communication with the first liquid reservoir 10 through a water inlet channel 41 of the liquid pump. A liquid outlet end of the liquid pump 40 is in communication with the liquid feeding nozzle 31 through a water outlet channel 42 of the liquid pump.

A control panel 51 is disposed at an upper portion of the housing 50. The control panel 51 allows the user to control the teeth cleaning apparatus 100 to turn on or turn off a teeth cleaning mode.

The ozone generator 60 is disposed in the first liquid reservoir, and is used for electrolyzing water to generate the teeth cleaning liquid containing ozone. The ozone generator 60 includes a first electrode 61, a second electrode 62, and a precious metal polymer 63 disposed between the first electrode 61 and the second electrode 62. The structure of the ozone generator is also known.

The controller 70 includes a pressure sensing module 71 and a control module 72. The pressure sensing module 71 is disposed on the connecting seat and configured to detect a pressure exerted by the teeth cleaner 20 on the connecting seat and send the pressure to the control module 72. The control module 72 is electrically connected to the pressure sensing module, the charging terminal 32, the liquid conveyer, the ozone generator 60, the power supply (not shown in the figure), and the control panel 51, and is configured to control the liquid conveyer as well as the ozone generator 60 to be turned on and turned off. The control module 72 is further provided with a BMS unit configured to manage charging of the rechargeable battery 213. In the present embodiment, it should be particularly noted that the control module 72 determines, according to the pressure exerted by the teeth cleaner 20 on the connecting seat and sent by the pressure sensing module 71, whether the second liquid reservoir 22 is fully filled up with the teeth cleaning liquid, so as to control the liquid conveyer to be turned off.

The teeth cleaning apparatus 100 in the present embodiment works in the following manner:

When teeth cleaning is not performed, the teeth cleaner 20 is placed on the connecting seat of the connector 30. The BMS unit of the control module 72 automatically controls charging for the rechargeable battery 213. Specifically, the power receiving terminal and the charging terminal 32 are in contact to implement an electric connection between the power supply and the rechargeable battery 213. At the same time, the projection 33 on the sidewall of the connector 30 is inserted into the exhaust hole 2232 to abut against the plug head 2234, so that the plug head 2234 overcomes an outward elastic force of the elastic piece 2237 and moves away from the exhaust hole 2232, and an interior of the second liquid reservoir 22 is then in communication with the atmosphere.

During teeth cleaning, the user first turns on the teeth cleaning mode through the control panel 51. The control module 72 controls the ozone generator 60 to be turned on, to electrolyze water to generate the teeth cleaning liquid containing ozone. After the ozone generator 60 operates for a period of time that is set manually, the control module 72 controls the liquid pump 40 to be turned on, and the teeth cleaning liquid in the first liquid reservoir 10 is transmitted to the second liquid reservoir 22 through the water inlet channel 41 of the liquid pump, the liquid pump 40, the water outlet channel 42 of the liquid pump, the liquid feeding nozzle 31, and the check valve 221. At this time, air in the second liquid reservoir 22 is exhausted quickly through the exhaust hole 2232, so that the second liquid reservoir 22 can be fully filled up quickly. After the second liquid reservoir 22 is fully filled, the pressure sensing module 71 sends a signal to the control module 72. After receiving the signal, the control module controls the liquid pump 40 to be turned off. At this time, the user can be informed that the teeth cleaner 20 is already fully filled up with the teeth cleaning liquid. Then, the user can remove the teeth cleaner 20 from the connecting seat, hold the teeth cleaner 20, and press the switch 211 on the teeth cleaner body 21. The teeth cleaning liquid in the second liquid reservoir 22 is output to the ejector 214 through the liquid suction pipe 212 and the liquid suction device 214, and is ejected from the ejector 214 to clean teeth.

In Embodiment 1, the ozone content can achieve a disinfection effect only when the teeth cleaning liquid containing ozone is prepared before teeth cleaning. However, water electrolysis requires high power, and cannot be directly performed in the teeth cleaner to prepare the teeth cleaning liquid. Therefore, the second liquid reservoir 22 is disposed, and is enabled to transmit the teeth cleaning liquid to the teeth cleaner body 21 during teeth cleaning. At the same time, when the teeth cleaner 20 is connected to the connector 30, the first liquid reservoir 10 transmits the teeth cleaning liquid to the second liquid reservoir 22 through the liquid pump 40, so that the teeth cleaning liquid can be generated and stored in the first liquid reservoir 10, and moreover, the teeth cleaning liquid in the first liquid reservoir 10 can be injected into the second liquid reservoir 22 automatically. Therefore, when the user cleans teeth, the teeth cleaning liquid is supplied from the second liquid reservoir 22 fixedly connected to the teeth cleaner body 21, so that the user can hold the teeth cleaner freely without being restricted by a hose, thereby obtaining good using experience.

Embodiment 2

Figure 5:
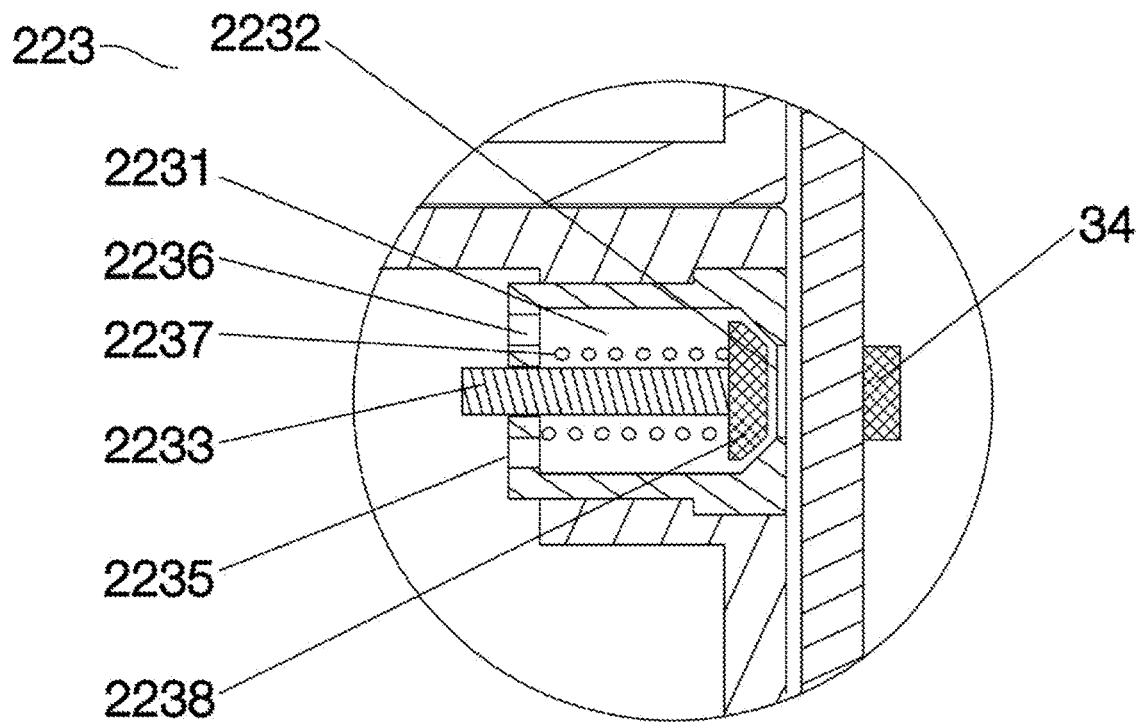
FIG. 5 is a partial schematic diagram of an exhaust structure and an exhaust driving structure in Embodiment 2.

The only difference between the teeth cleaning apparatus 100 in Embodiment 2 and the teeth cleaning apparatus 100 in Embodiment 1 lies in a different exhaust structure 223 on the second liquid reservoir 22 and a different exhaust driving structure on the sidewall of the connector. Referring to FIG. 5, as shown in FIG. 5, in Embodiment 2, the exhaust structure 223 on the second liquid reservoir 22 includes an exhaust passage 2231 provided with an exhaust hole 2232, a slide bar 2233 slidably disposed in the exhaust passage 2231, a first magnetic element 2238 fixedly connected at one end of the slide bar 2233 and used for blocking the exhaust hole 2232, and an elastic piece 2237 for driving the first magnetic element 2238 to block the exhaust hole 2232. The exhaust hole 2232 is provided on an outer side of the exhaust passage 2231, and a stopping wall 2235 is provided on an inner side of the exhaust passage 2231. The stopping wall 2235 is provided with a through hole 2236. The slide bar 2233 penetrates the stopping wall 2235. The elastic piece 2237 is a spring sleeved over the slide bar 2233. One end of the elastic piece 2237 abuts against the stopping wall 2235, and the other end of the elastic piece 2237 abuts against the first magnetic element 2238. In the present embodiment, an external wall of the housing 50 forms the sidewall of the connector 30. The exhaust driving structure is specifically a second magnetic element 34 located on the sidewall of the connector 30. The teeth cleaner 20 is placed on the connecting seat. Due to the effect that like poles repel, the second magnetic element 34 drives the approaching first magnetic element 2238 to overcome an elastic force of the elastic piece 2237 and move away from the exhaust hole 2232, so that the interior of the second liquid reservoir is in communication with the atmosphere. Definitely, the same effect can also be achieved if the positions of the exhaust hole 2232 and the stopping wall 2235 are swapped and the second magnetic element 34 is set to attract the first magnetic element 2238.

Embodiment 3

Figure 6:
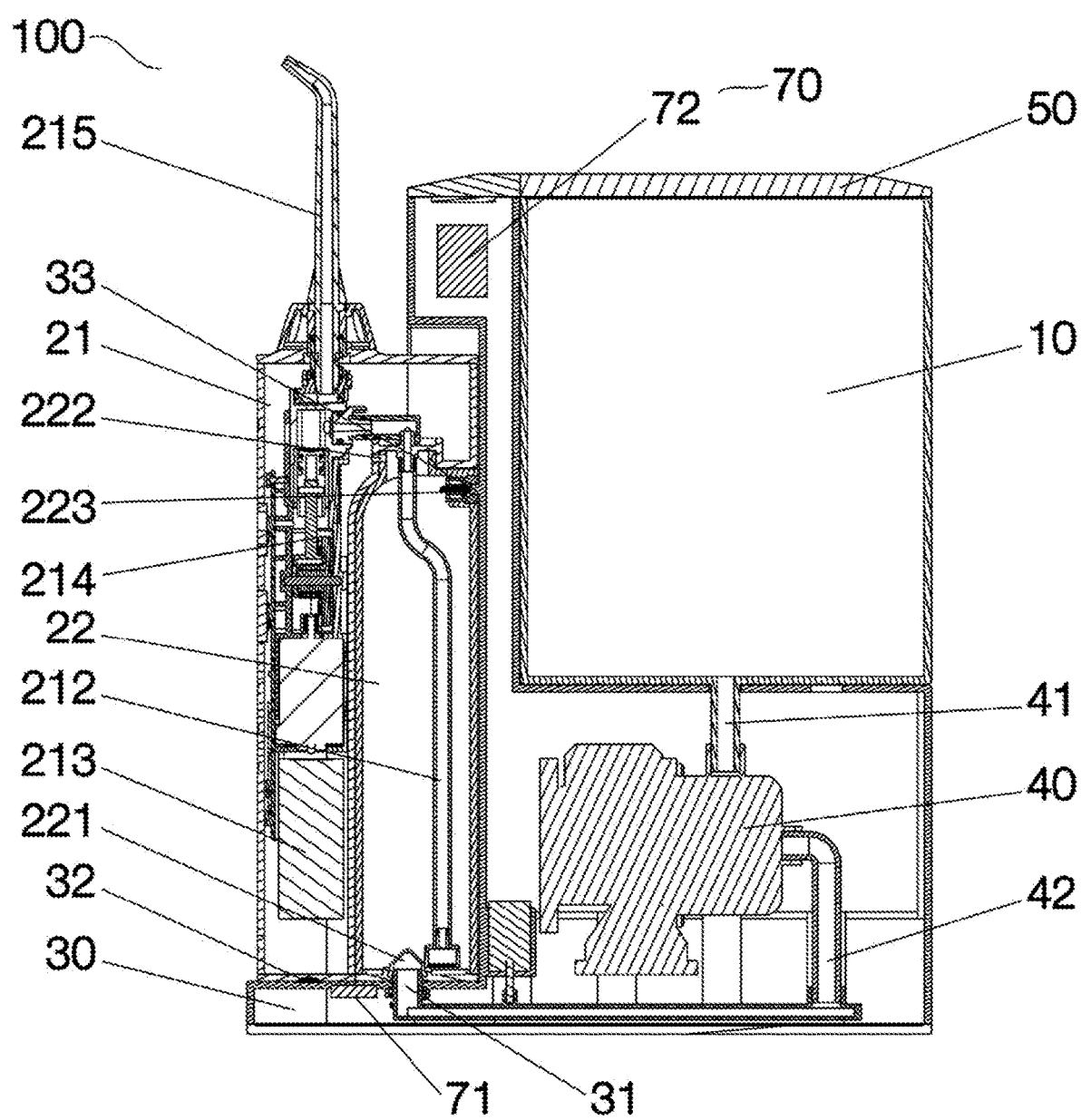
FIG. 6 is a schematic structural diagram of a teeth cleaning apparatus in Embodiment 3.

Referring to FIG. 6, different from Embodiment 1, the teeth cleaning apparatus 100 in Embodiment 3 does not include the ozone generator 60, and the first liquid reservoir 10 is used to store the teeth cleaning liquid being blended, or filtered purified water, or any teeth cleaning liquid that has a disinfection effect and can be put into a mouth. In this case, different from Embodiment 1, when the teeth cleaner 20 is placed on the connecting seat, the pressure sensing module 71 sends a seating signal to the control module 72, and the control module 72 controls the liquid conveyer (which is also the liquid pump 40 in Embodiment 2) to be turned on, so as to inject teeth cleaning liquid into the second liquid reservoir 22. The control module 72 controls the liquid conveyer to be turned off until the second liquid reservoir 22 is fully filled. At this time, the user does not need to turn on the teeth cleaning mode through the control panel 51, and only needs to remove the teeth cleaner 20 from the connector 30 to clean teeth.

It can be learned from Embodiment 3 that, although the technical solution in this application is mainly used for improving the convenience of holding the teeth cleaner in the case where the teeth cleaning liquid needs to be prepared right before teeth cleaning, the technical solution can also be used in the case where the teeth cleaning liquid does not need to be prepared right before teeth cleaning. In other words, even if the teeth cleaning liquid does not need to be prepared right before teeth cleaning, the teeth cleaning apparatus 100 still has an important beneficial effect, because a volume of the teeth cleaning liquid stored by the first liquid reservoir 10 is larger than a volume required for one teeth cleaning process, and the teeth cleaning apparatus 100 can automatically fully fill the second liquid reservoir 20. The user does not need to specially prepare the teeth cleaning liquid each time before teeth cleaning, and does not need to manually inject the teeth cleaning liquid into the second liquid reservoir 20 inconveniently.

Embodiment 4

The difference between Embodiment 4 and Embodiment 3 lies in the first liquid reservoir 10, the liquid conveyer, and the exhaust structure 223 on the second liquid reservoir 22; moreover, there is no exhaust driving structure in Embodiment 4.

Figure 7:
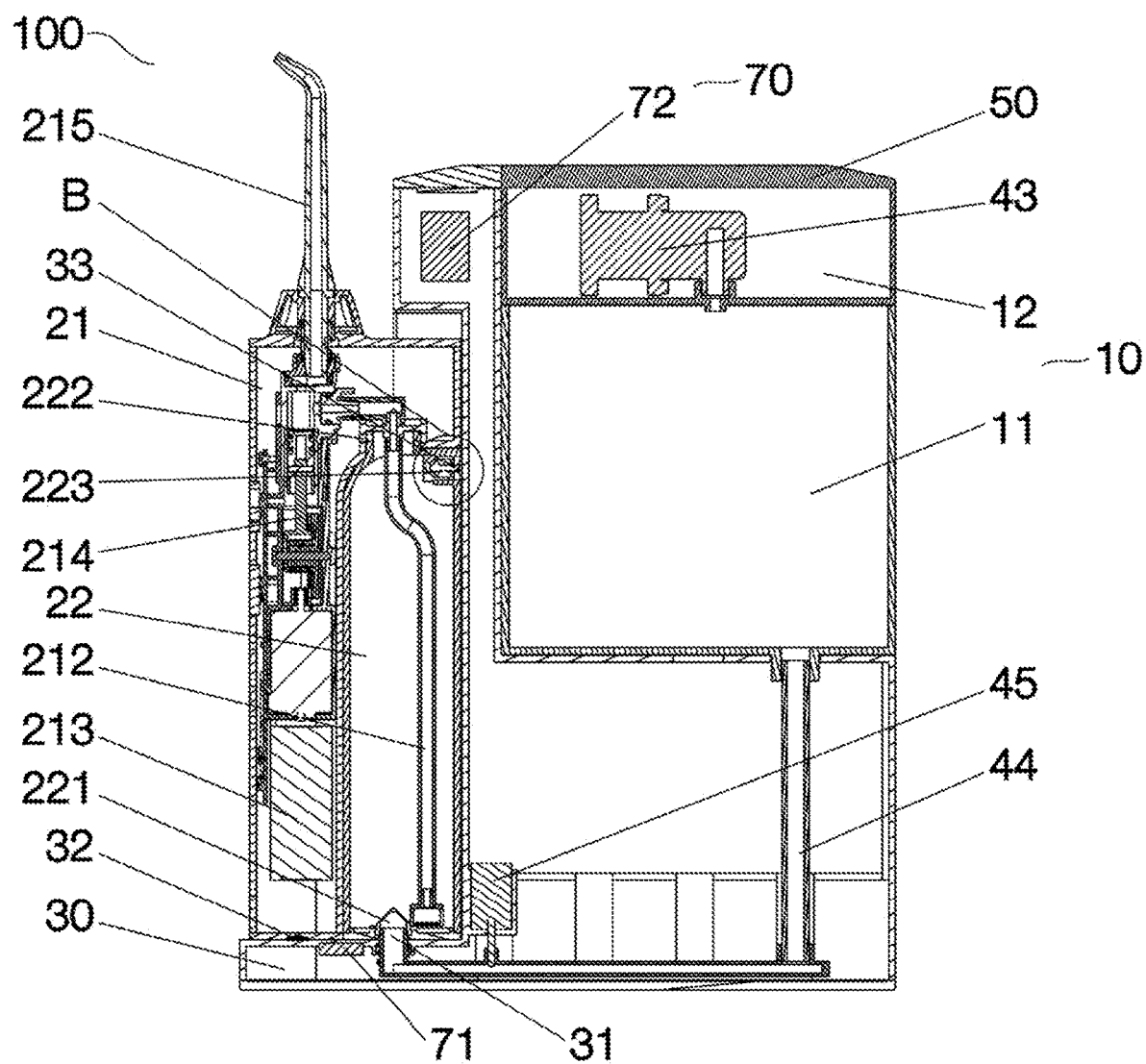
FIG. 7 is a schematic structural diagram of a teeth cleaning apparatus in Embodiment 4.

As shown in FIG. 7, in Embodiment 4, the first liquid reservoir 10 includes a liquid storage cavity 11 and a gas inlet cavity 12. In the present embodiment, the liquid conveyer is a gas booster pump 43. A gas inlet end of the gas booster pump 43 is disposed in the gas inlet cavity 12 and a gas outlet end of the gas booster pump 43 is disposed in the liquid storage cavity 11. The gas booster pump 43 boosts pressure of air in the liquid storage cavity 11 to transmit the teeth cleaning liquid to the liquid feeding nozzle 31. In the present embodiment, the liquid storage cavity 11 is in communication with the liquid feeding nozzle 31 through a water passing channel 44. A switch valve 45 is disposed on the water passing channel 44 and is used for controlling opening and closing of the water passing channel 44. In the present embodiment, the switch valve 45 and the gas booster pump 43 are both electrically connected to the control module 72.

Figure 8:
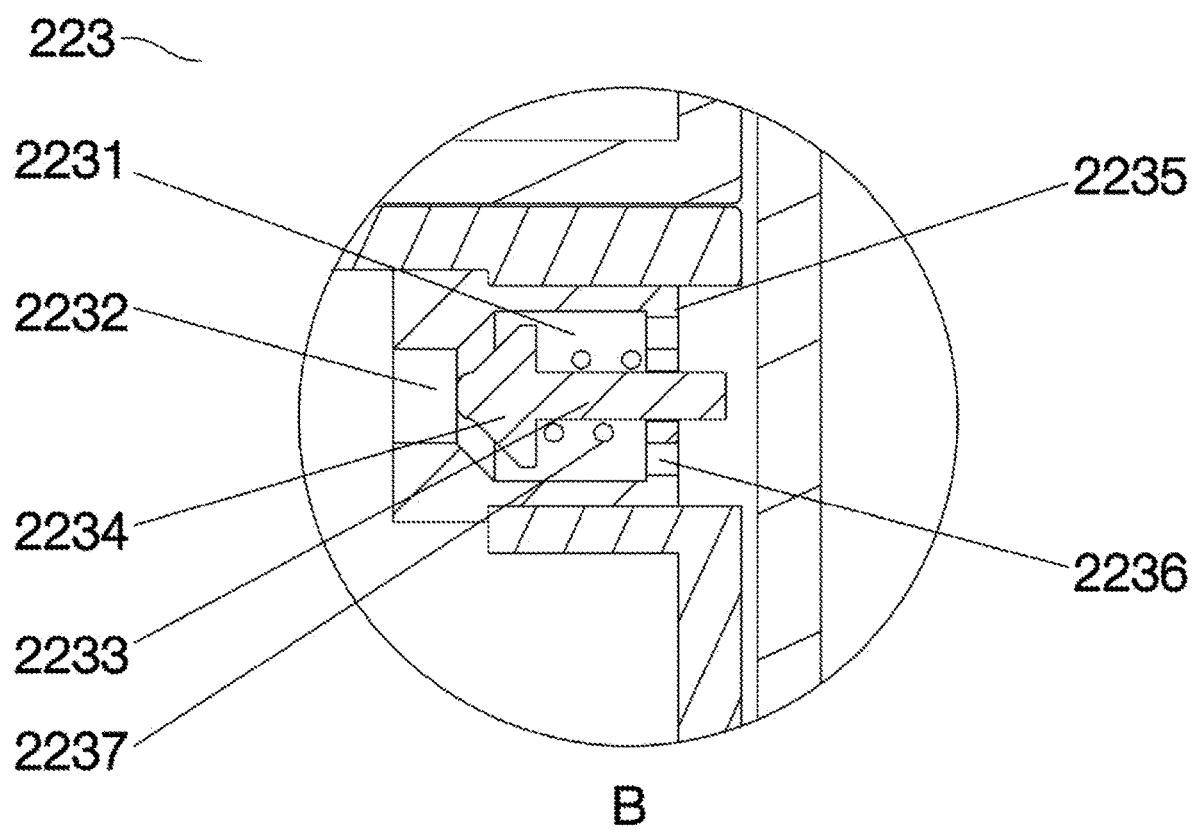
FIG. 8 in an enlarged view of part B in FIG. 7, and shows an exhaust structure in Embodiment 4.

Referring to FIG. 8, in Embodiment 4, the exhaust structure 223 includes an exhaust passage 2231 provided with an exhaust hole 2232, a slide bar 2233 slidably disposed in the exhaust passage 2231, a plug head 2234 fixedly connected at one end of the slide bar 2233 and used for blocking the exhaust hole 2232, and an elastic piece 2237 for driving the plug head 2234 to block the exhaust hole 2232. The elastic piece 2237 is configured as a spring. In the present embodiment, the exhaust hole 2232 is provided at an inner end of the exhaust passage 2231, and a stopping wall 2235 is provided at an outer end of the exhaust passage 2231. The stopping wall 2235 is provided with a through hole 2236. The slide bar 2233 penetrates the stopping wall 2235. The elastic piece 2237 is sleeved over the slide bar 2233. One end of the elastic piece 2237 abuts against the stopping wall 2235 and the other end of the elastic piece 2237 abuts against the plug head 2234.

When the user places the teeth cleaner 20 on the connecting seat, the pressure sensing module 71 sends a seating signal to the control module 72, and the control module 72 controls the liquid conveyer and the switch valve 44 to be turned on, to inject the teeth cleaning liquid into the second liquid reservoir 22. At this time, an air pressure in the second liquid reservoir 22 rises gradually as the liquid is injected, until the plug head 2234 overcomes an elastic force of the elastic piece 2237 and moves away from the exhaust hole 2232, so that the interior of the second liquid reservoir 22 is in communication with the atmosphere. After the second liquid reservoir 22 is fully filled, the controller 72 controls the gas booster pump 43 and the switch valve 44 to be turned off.

Therefore, it can be learned that the liquid conveyer may be any apparatus or mechanism that is known prior to the filing date and capable of transmitting the teeth cleaning liquid in the first liquid reservoir 10 to the teeth cleaner 20. In addition, the liquid conveyer is not necessarily combined with the first liquid reservoir 10, and may be a part of the teeth cleaner 20. For example, the second liquid reservoir 22 is vacuumized, so that the teeth cleaning liquid is transmitted from the first liquid reservoir 21 to the second liquid reservoir 22 through the liquid feeding nozzle 31.

What is claimed is:

1. A teeth cleaning apparatus, comprising:
    a first liquid reservoir, used for storing a teeth cleaning liquid;
    a teeth cleaner, including a teeth cleaner body and a second liquid reservoir fixedly connected to the teeth cleaner body, the second liquid reservoir transmitting the teeth cleaning liquid to the teeth cleaner body during teeth cleaning, and the second liquid reservoir being further provided with a check valve that is opened when the teeth cleaning liquid is injected into the second liquid reservoir;
    a connector, which is separated from the teeth cleaner during teeth cleaning, and allows the teeth cleaner to be connected thereon after teeth cleaning, the connector being provided with a liquid feeding nozzle, and the liquid feeding nozzle being in communication with the second liquid reservoir through the check valve when the connector is connected to the teeth cleaner; and
    a liquid conveyer, used for transmitting the teeth cleaning liquid in the first liquid reservoir to the second liquid reservoir through the liquid feeding nozzle,
    wherein the connector includes a connecting seat that allows the teeth cleaner to be placed thereon, and the teeth cleaning apparatus further comprises a controller configured to control the liquid conveyer to be turned on and turned off, wherein the controller includes a pressure sensing module and a control module; the pressure sensing module is disposed on the connecting seat, to detect a pressure exerted by the teeth cleaner on the connecting seat and send the pressure to the control module; and the control module determines, according to the pressure exerted by the teeth cleaner on the connecting seat, whether the second liquid reservoir is fully filled with the teeth cleaning liquid, so as to control the liquid conveyer to be turned off.

2. The teeth cleaning apparatus according to claim 1, further comprising an ozone generator that is disposed in the first liquid reservoir.

3. The teeth cleaning apparatus according to claim 2, wherein the liquid conveyer is a liquid pump, one end of the liquid pump is in communication with the first liquid reservoir, and the other end of the liquid pump is in communication with the liquid feeding nozzle.

4. The teeth cleaning apparatus according to claim 2, wherein the liquid conveyer is a gas booster pump, the gas booster pump is disposed in the first liquid reservoir, and transmits the teeth cleaning liquid to the liquid feeding nozzle by boosting air in the first liquid reservoir.

5. The teeth cleaning apparatus according to claim 2, wherein the second liquid reservoir is further provided with an air inlet, so that air flows in when the second liquid reservoir transmits the teeth cleaning liquid to the teeth cleaner body.

6. The teeth cleaning apparatus according to claim 2, wherein the second liquid reservoir is further provided with an exhaust structure at an upper portion thereof; and
    the exhaust structure comprises an exhaust passage provided with an exhaust hole, a slide bar slidably disposed in the exhaust passage, a plug head fixedly connected at one end of the slide bar and used for blocking the exhaust hole, and an elastic piece for driving the plug head to block the exhaust hole; the teeth cleaning liquid is injected to the second liquid reservoir, so that an air pressure in the second liquid reservoir rises to drive the plug head to overcome an elastic force of the elastic piece and move away from the exhaust hole, and thus an interior of the second liquid reservoir is in communication with an atmosphere.

7. The teeth cleaning apparatus according to claim 1, wherein the liquid conveyer is a liquid pump, one end of the liquid pump is in communication with the first liquid reservoir, and the other end of the liquid pump is in communication with the liquid feeding nozzle.

8. The teeth cleaning apparatus according to claim 1, wherein the liquid conveyer is a gas booster pump, the gas booster pump is disposed in the first liquid reservoir, and transmits the teeth cleaning liquid to the liquid feeding nozzle by boosting air in the first liquid reservoir.

9. The teeth cleaning apparatus according to claim 1, wherein the second liquid reservoir is further provided with an air inlet, so that air flows in when the second liquid reservoir transmits the teeth cleaning liquid to the teeth cleaner body.

10. The teeth cleaning apparatus according to claim 1, wherein a rechargeable battery is disposed in the teeth cleaner body; a charging terminal electrically connected to a power supply is disposed at a bottom portion of the connecting seat; and when the teeth cleaner is placed on the connecting seat, the charging terminal is electrically connected to the rechargeable battery to charge the rechargeable battery.

11. The teeth cleaning apparatus according to claim 1, wherein the second liquid reservoir is further provided with an exhaust structure at an upper portion thereof; and the exhaust structure comprises an exhaust passage provided with an exhaust hole, a slide bar slidably disposed in the exhaust passage, a plug head fixedly connected at one end of the slide bar and used for blocking the exhaust hole, and an elastic piece for driving the plug head to block the exhaust hole; the teeth cleaning liquid is injected to the second liquid reservoir, so that an air pressure in the second liquid reservoir rises to drive the plug head to overcome an elastic force of the elastic piece and move away from the exhaust hole, and thus an interior of the second liquid reservoir is in communication with an atmosphere.

12. The teeth cleaning apparatus according to claim 1, wherein the second liquid reservoir is further provided with an exhaust structure at an upper portion thereof; the connector is further provided with a sidewall, and the sidewall is further provided with an exhaust driving structure; and when the teeth cleaner is placed on the connecting seat, the exhaust driving structure on the sidewall of the connector drives the exhaust structure to be opened, so that an interior of the second liquid reservoir is in communication with an atmosphere.

13. The teeth cleaning apparatus according to claim 12, wherein the exhaust structure includes an exhaust passage provided with an exhaust hole, a slide bar slidably disposed in the exhaust passage, a first magnetic element fixedly connected at one end of the slide bar and used for blocking the exhaust hole, and an elastic piece for driving the first magnetic element to block the exhaust hole; the exhaust driving structure includes a second magnetic element provided on the sidewall of the connector; and when the teeth cleaner is placed on the connecting seat, the second magnetic element drives the approaching first magnetic element to overcome an elastic force of the elastic piece and move away from the exhaust hole, so that the interior of the second liquid reservoir is in communication with the atmosphere.

14. The teeth cleaning apparatus according to claim 12, wherein the exhaust structure further includes an exhaust passage provided with an exhaust hole, a slide bar slidably disposed in the exhaust passage, a plug head fixedly connected at one end of the slide bar and used for blocking the exhaust hole, and an elastic piece for driving the plug head to block the exhaust hole; the exhaust driving structure includes a projection provided on the sidewall of the connector; when the teeth cleaner is placed on the connecting seat, the projection abuts against the plug head and drives the plug head to overcome an elastic force of the elastic piece and move away from the exhaust hole, so that the interior of the second liquid reservoir is in communication with the atmosphere.

15. A teeth cleaning apparatus, comprising:

a first liquid reservoir, used for storing a teeth cleaning liquid;

a teeth cleaner, including a teeth cleaner body and a second liquid reservoir fixedly connected to the teeth cleaner body, the second liquid reservoir transmitting the teeth cleaning liquid to the teeth cleaner body during teeth cleaning, and the second liquid reservoir being further provided with a check valve that is opened when the teeth cleaning liquid is injected into the second liquid reservoir;

a connector, which is separated from the teeth cleaner during teeth cleaning, and allows the teeth cleaner to be connected thereon after teeth cleaning, the connector being provided with a liquid feeding nozzle, and the liquid feeding nozzle being in communication with the second liquid reservoir through the check valve when the connector is connected to the teeth cleaner; and a liquid conveyer, used for transmitting the teeth cleaning liquid in the first liquid reservoir to the second liquid reservoir through the liquid feeding nozzle, wherein the connector includes a connecting seat that allows the teeth cleaner to be placed thereon, and the second liquid reservoir is further provided with an exhaust structure at an upper portion thereof; the connector is further provided with a sidewall, and the sidewall is further provided with an exhaust driving structure; and when the teeth cleaner is placed on the connecting seat, the exhaust driving structure on the sidewall of the connector drives the exhaust structure to be opened, so that an interior of the second liquid reservoir is in communication with an atmosphere.

16. The teeth cleaning apparatus according to claim 15, wherein the exhaust structure includes an exhaust passage provided with an exhaust hole, a slide bar slidably disposed in the exhaust passage, a first magnetic element fixedly connected at one end of the slide bar and used for blocking the exhaust hole, and an elastic piece for driving the first magnetic element to block the exhaust hole; the exhaust driving structure includes a second magnetic element provided on the sidewall of the connector; and when the teeth cleaner is placed on the connecting seat, the second magnetic element drives the approaching first magnetic element to overcome an elastic force of the elastic piece and move away from the exhaust hole, so that the interior of the second liquid reservoir is in communication with the atmosphere.

17. The teeth cleaning apparatus according to claim 15, wherein the exhaust structure further includes an exhaust passage provided with an exhaust hole, a slide bar slidably disposed in the exhaust passage, a plug head fixedly connected at one end of the slide bar and used for blocking the exhaust hole, and an elastic piece for driving the plug head to block the exhaust hole; the exhaust driving structure includes a projection provided on the sidewall of the connector; when the teeth cleaner is placed on the connecting seat, the projection abuts against the plug head and drives the plug head to overcome an elastic force of the elastic piece and move away from the exhaust hole, so that the interior of the second liquid reservoir is in communication with the atmosphere.

* * * * *